(12) United States Patent
Smith et al.

(10) Patent No.: US 7,587,942 B2
(45) Date of Patent: Sep. 15, 2009

(54) ULTRASONIC INSPECTION CRAWLER AND METHOD FOR INSPECTING WELDS OF JET PUMPS IN A NUCLEAR REACTOR VESSEL

(75) Inventors: Brandon L. Smith, Watha, NC (US); Richard Hatley, Morristown, NJ (US); Kenneth Hatley, Madison, NJ (US)

(73) Assignee: General Electric Company, Schenectady, NY (US)

( * ) Notice: Subject to any disclaimer, the term of this patent is extended or adjusted under 35 U.S.C. 154(b) by 336 days.

(21) Appl. No.: 11/564,415

(22) Filed: Nov. 29, 2006

(65) Prior Publication Data
US 2008/0121041 A1    May 29, 2008

(51) Int. Cl.
*G01N 29/265* (2006.01)

(52) U.S. Cl. .............. 73/622; 73/865.8; 73/866.5; 376/249

(58) Field of Classification Search .......... 73/865.8, 73/866.5, 622, 623; 376/249
See application file for complete search history.

(56) References Cited

U.S. PATENT DOCUMENTS

| | | | | |
|---|---|---|---|---|
| 3,809,607 A | * | 5/1974 | Murray et al. | 376/249 |
| 4,304,133 A | * | 12/1981 | Feamster, III | 73/633 |
| 4,330,865 A | * | 5/1982 | Hyde et al. | 376/249 |
| 5,128,094 A | * | 7/1992 | Muller et al. | 376/249 |
| 5,473,953 A | * | 12/1995 | Appel | 73/866.5 |
| 6,904,817 B2 | * | 6/2005 | Davis et al. | 73/865.8 |
| 7,201,055 B1 | * | 4/2007 | Bagley et al. | 73/618 |
| 2008/0087112 A1 | * | 4/2008 | Bagley et al. | 73/865.8 |
| 2008/0087113 A1 | * | 4/2008 | Bagley et al. | 73/865.8 |

FOREIGN PATENT DOCUMENTS

DE   3916186 A1 * 11/1990
JP   09005306 A  *  1/1997

* cited by examiner

*Primary Examiner*—Hezron Williams
*Assistant Examiner*—Rose M Miller
(74) *Attorney, Agent, or Firm*—Nixon & Vanderhye P.C.

(57) ABSTRACT

An inspection assembly adapted to traverse an inspection surface, the assembly includes: a crawler body including a first side and a bottom side, wherein the first side is adapted to face a first inspection surface and the bottom side is adapted to engage a second inspection surface separated from the first inspection surface by a gap; a suction module in the crawler body adapted to create a suction between the first inspection surface to bias the crawler body against the first inspection surface; at least one roller mounted in the crawler body adapted to engage the first inspection surface, and at least one mast having a mount to receive a sensor, wherein said mast extendable from the crawler body into the gap.

20 Claims, 9 Drawing Sheets

ULTRASONIC INSPECTION CRAWLER AND METHOD FOR INSPECTING WELDS OF JET PUMPS IN A NUCLEAR REACTOR VESSEL

BACKGROUND

The invention disclosed herein relates generally to inspection of using robots and in particular to inspection of welds of jet pump diffusers and jet pump adapters in boiling water nuclear reactors (BWRs).

BWRs typically include jet pumps that participate in recirculating water through the reactors. An array of jet pumps are generally located around the circumferential periphery of the reactor vessel in the BWR. In a typical BWR, there are commonly ten jet pumps each with a pair of diffusers that direct water to the jet pump. Each of the twenty diffusers is attached to or extend past a horizontal baffle plate between the reactor vessel wall and a outer wall of the reactor. While many BWRs have jet pump diffusers that are welded directly to the baffle plates, some reactors attach the jet pump diffusers to an adapter located below the baffle plate. The inspection crawler and method disclosed herein may be used to inspect welds of jet pump diffusers that extend down past the baffle plate.

Inspection of the welds between the adapter and diffusers is needed to monitor the integrity of the diffusers and water recirculation system. Inspecting welds of the adapter and diffuser requires an inspection scanner to traverse a narrow gap between the baffle plate and diffuser. The narrow gap has been problematic in inserting ultrasonic inspection scanners down passed the baffle plate to inspect the welds attaching the adapter and diffuser. There is a long felt need for devices to inspect welds of diffusers below a baffle plate.

SUMMARY

An inspection assembly has been developed that is adapted to traverse an inspection surface, the assembly includes: a crawler body including a first side and a bottom side, wherein the first side is adapted to face a first inspection surface and the bottom side is adapted to engage a second inspection surface separated from the first inspection surface by a gap; a suction module in the crawler body adapted to create a suction between the first inspection surface to bias the crawler body against the first inspection surface; at least one roller mounted in the crawler body adapted to engage the first inspection surface, and at least one mast having a mount to receive a sensor, wherein said mast extendable from the crawler body into the gap.

The sensor may be an ultrasonic transducer for weld inspections. The first inspection surface may be upright and circular in cross-section, and the second inspection surface may be substantially horizontal. The crawler body may include a driver module having at least one driver roller extending through the first side of the crawler body and adapted to engage the first inspection surface. Further, the suction module may include an impeller adapted to create a suction between the first side of the crawler body and the first inspection surface. A tracking wheel may be mounted on the crawler body and an encoder may generate a signal indicative of displacement of the tracking wheel across the second inspection surface.

An inspection assembly has been developed that is adapted to inspect welds associated with a diffuser in a jet pump in a boiling water nuclear reactor (BWR), the assembly comprising: a crawler housing including a first side surface and a bottom surface, wherein the first side surface faces a side surface of the diffuser and the bottom surface faces a baffle plate of the BWR; a suction device in the first side surface adapted to create a suction between the first side surface and a surface of the diffuser to bias the crawler body against the diffuser, and at least one mast having a mount to receive a sensor and said mast is supported by crawler housing.

A method has been developed for inspecting weld joints in a gap between an generally horizontal surface and a generally upright surface using a robotic crawler including a crawler body having at least one mast and a sensor mounted on the mast, the method comprises: positioning the crawler body on the horizontal surface and against the upright surface; establishing a suction between the crawler body and upright surface to seat the body against the upright surface; extending the mast and sensor into the gap below the crawler body; moving the crawler body across the horizontal surface while the suction seats the body against the upright surface, and sensing a condition in the gap with the sensor and conveying signals from the sensor to a control unit.

DETAILED DESCRIPTION

Figure 1:
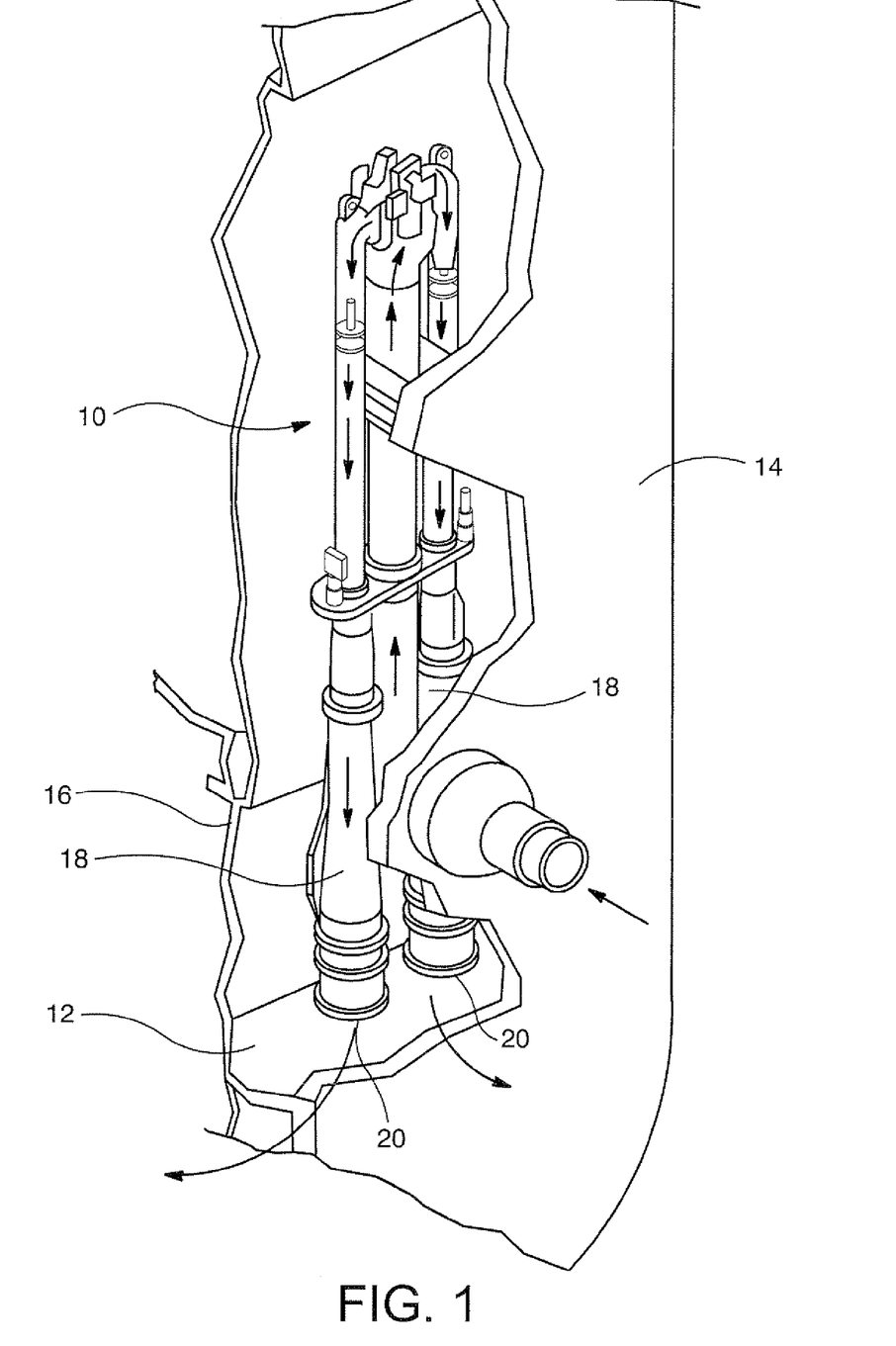
FIG. 1 is a perspective view of a boiling water reactor (BWR) with a cut away region to show exemplary jet pumps having diffuser shrouds and an adapter.

FIG. 1 is a perspective view of a BWR with a cut-away view to show a jet pump assembly 10 which is mounted on a baffle plate 12 between the wall 14 of the reactor pressure vessel and inner reactor core 16. The jet pump assembly includes a pair of diffusers 18 that extend through an aperture 20 in the baffle plate.

Figure 2:
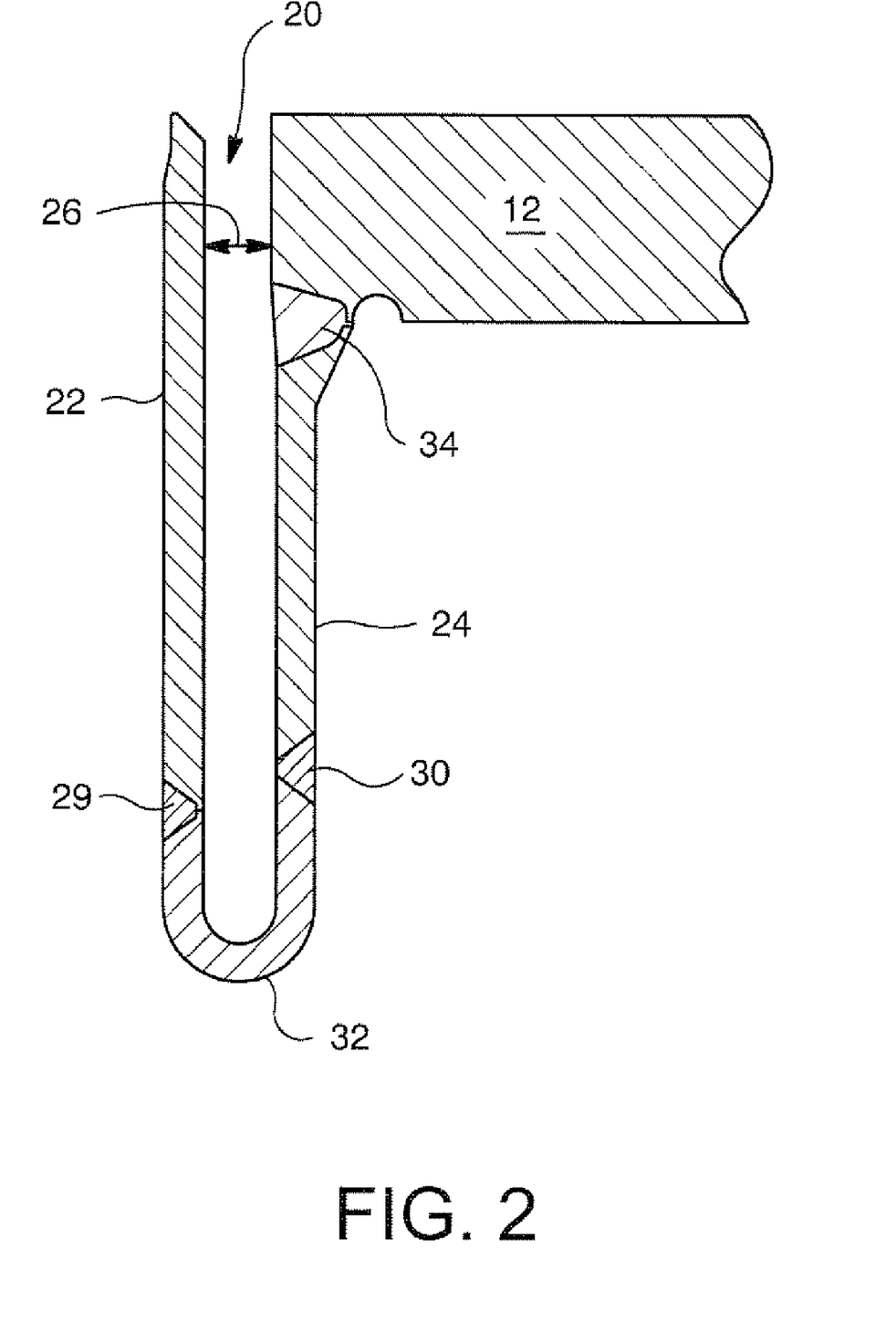
FIG. 2 is an enlarged cross-sectional view of a portion of a diffuser, an edge of a baffle plate and the adapter joining the tail pipe to the baffle plate.

FIG. 2 is a cross-sectional side, enlarged view of an edge of the baffle plate 12, a diffuser conical tail pipe 22 and an adapter ring 24 connecting the tail pipe to the baffle plate. The adapter ring 24 drops the base of the diffuser tail pipe below the baffle plate. An annular gap 26 exists below the baffle plate and extends between the outer diffuser wall on one side and the baffle plate and adapter ring on the other side. A U-joint 32 at the bottom of the gap 26 joins the adapter ring to the diffuser 22.

The aperture 20 in the baffle plate is defined by a circular edge of the baffle plate around the aperture. A narrow, annular gap 26 exists between the aperture edge of the baffle plate and the cylindrical side wall of the tail pipe 22. Deep down in the gap 26 are a pair of annular welds, which include a weld 28 that joins the tail pipe 22 to an annular U-joint 32 and the weld 30 that joins the U-joint 32 to the annular adapter ring 24. These welds 28, 30 require periodic inspection, but are deep in the gap 26 and difficult to reach with conventional weld inspection scanners. Another annular weld 34 joints the adapter ring 24 to the baffle plate 12, is near the surface of the baffle plate.

In the annular gap 26, the ultrasonic sensing heads must be inserted to inspect the welds 28, 30 and 34 that extend circumferentially around the diffuser and adapter ring. The welds are in the tight annular gap 26 below the baffle plate and around the periphery of the diffuser. It is difficult to insert ultrasonic sensing units to this annular gap. There is a long felt need for an ultrasonic inspection tool that can inspect the welds below the baffle plate that attach the diffuser of a jet pump to the adapter that connects the jet pump to the baffle plate.

Figure 3:
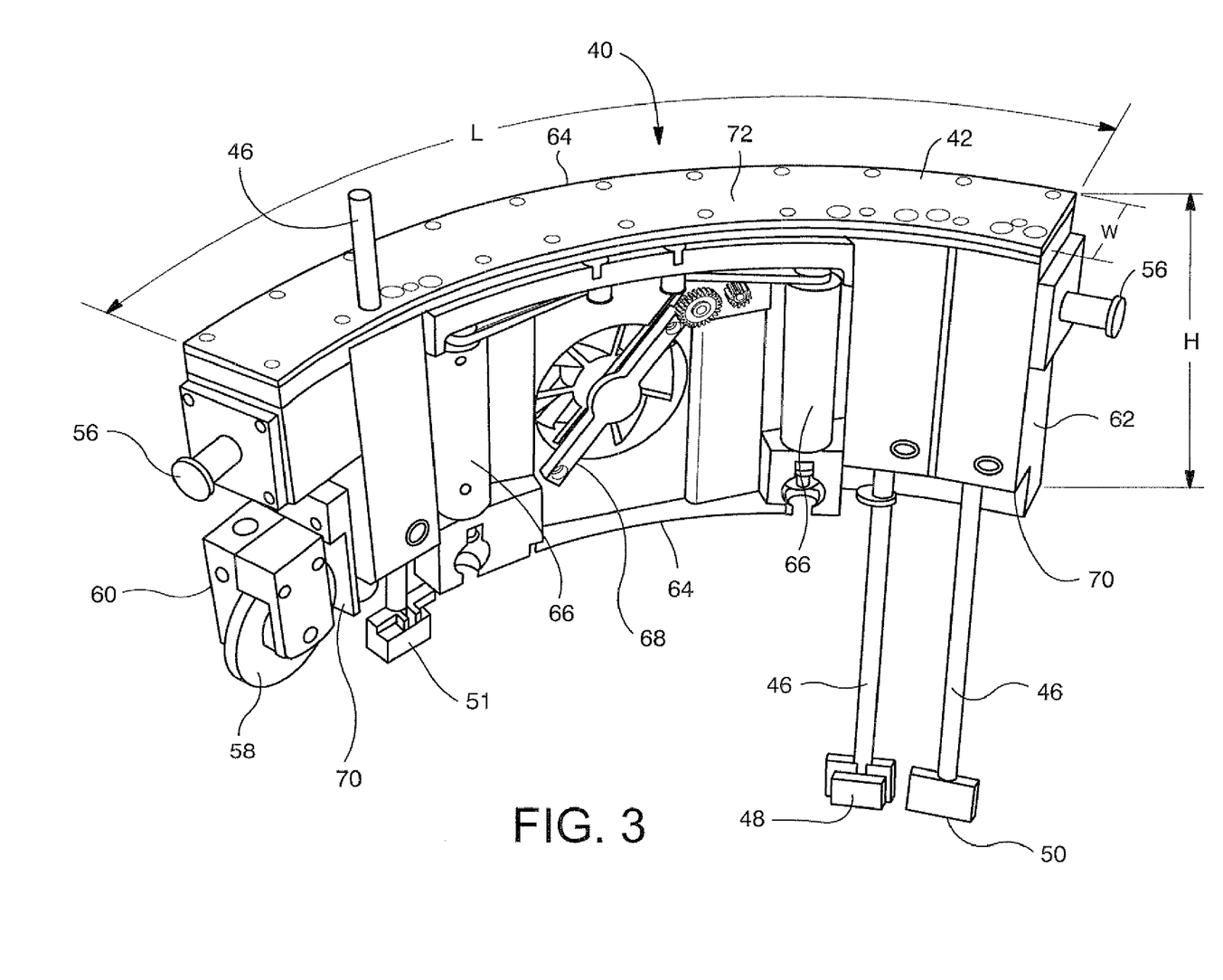
FIG. 3 is a perspective view of a crawler for inspecting welds between the diffuser tail pipe, adapter and baffle plate.
Figure 4:
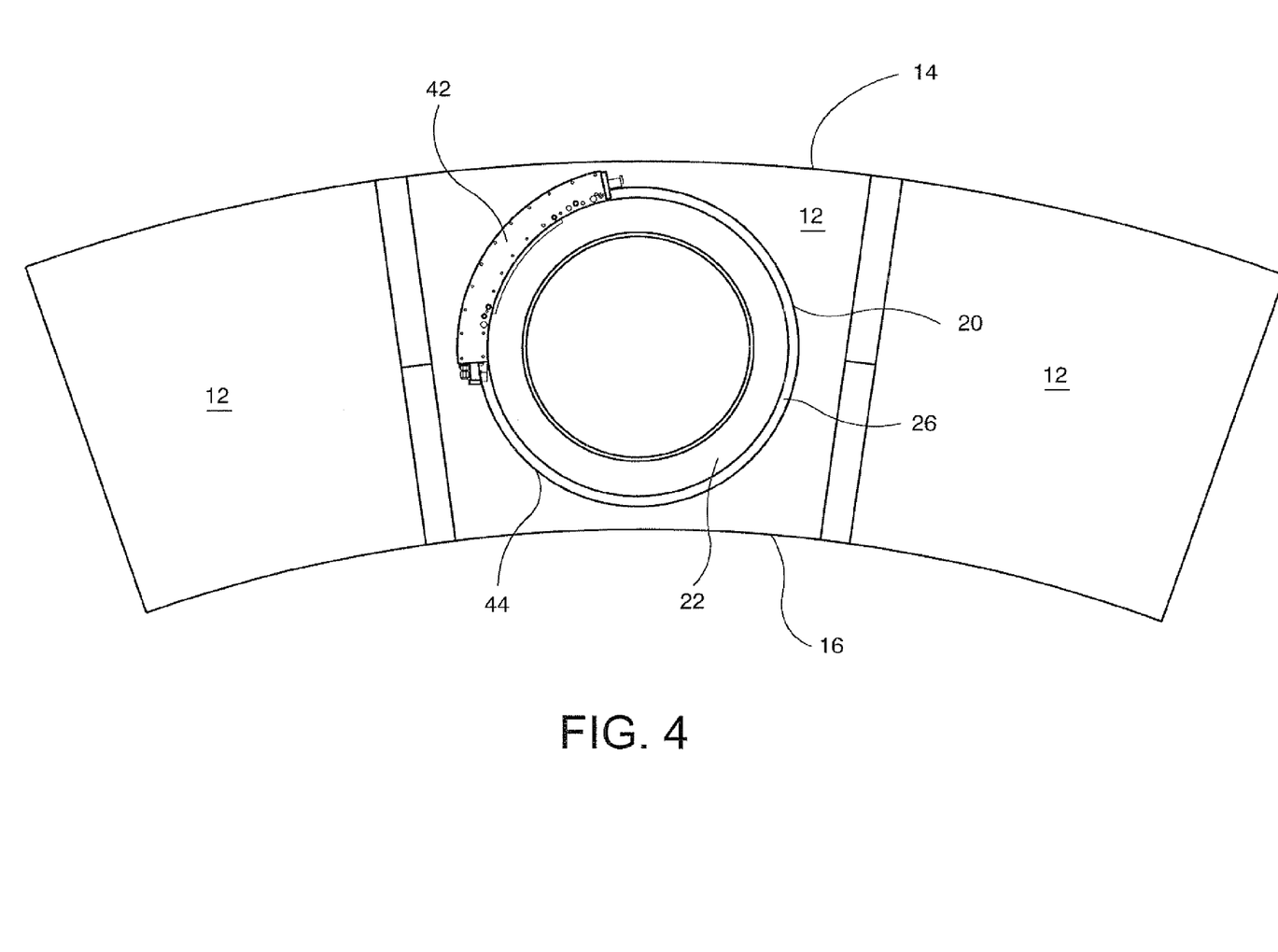
FIG. 4 is a top down view of a crawler circumnavigating the perimeter of a diffuser and traversing a baffle plate.

FIG. 3 is a perspective view of a robotic weld inspection tool 40 has been developed that includes an arc-shaped crawler body 42 which traverses the baffle plate 14 as it circumnavigates a diffuser tail pipe 22. The crawler device driven circumferentially around the diffuser 18. FIG. 4 is a top down view of a crawler body 42 leaning against a tail pipe 22 as it moves in a circular path 44 on the baffle plate 12 and around the tail pipe.

The crawler 40 includes multiple sensor masts 46 that may be extended down from the crawler body 42. The masts extend into the annular gap 26 between the baffle plate aperture 20 and outer sidewall of the diffuser tail pipe 22. The masts 46 support ultrasonic transducer units 48, 50 that transmit ultrasonic signals at welds 28, 30 and receives reflected signals from the welds and surrounding joined structures. The transducer units may be alternatively Eddy current transducers and imaging devices, e.g., a video camera. Further, the transducer units may have multiple types of sensors, such as one or more of an ultrasonic transducer, an Eddy current sensor and a video camera.

The masts 46 extend the transducer units down in the gap 26 until each unit is adjacent a corresponding weld. For example, the transducer head of unit 48 faces outward towards the outer weld 28 between the tail pipe diffuser and U-joint and the transducer head of unit 50 faces inward towards the inner weld 30 between the U-joint and adapter ring 24. A third (optional) transducer head 51 may be positioned adjacent the weld 34 between the adapter ring and baffle plate.

Figure 5:
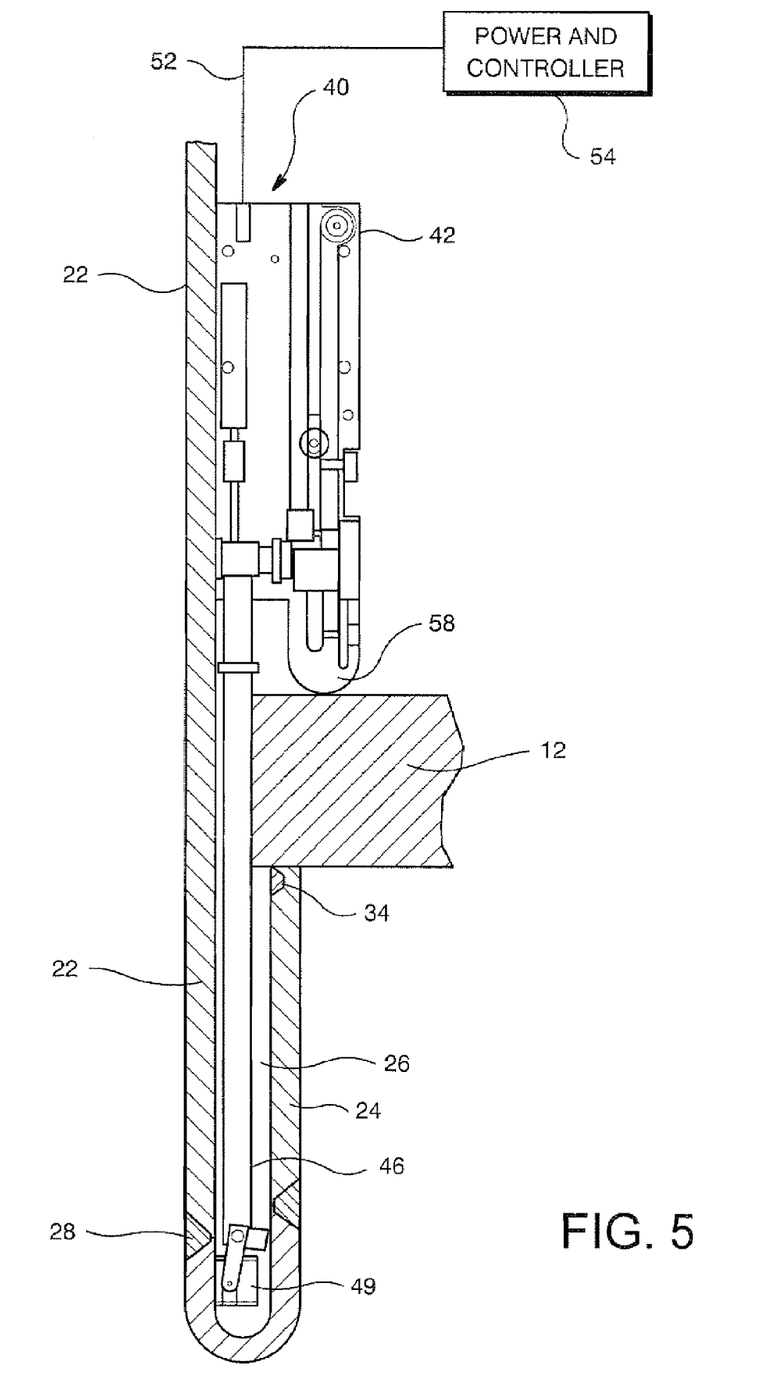
FIG. 5 is a side view of a crawler seated on a baffle plate and against a diffuser with a mast projecting a scanner transducer between the diffuser tail pipe and adapter to inspect welds.

FIG. 5 shows the crawler 40 with the crawler body 42 leaning against the sidewall of the diffuser tail pipe 22 and riding on the upper surface of the baffle plate 12. The crawler body extends the respective masts 46 down into the gap 26. (only the mast for transducer unit 48 is shown in FIG. 5 for illustrative purposes).

The crawler body extends the transducer unit 48 down to the weld 28 to be inspected. The crawler may extend the transducer unit down a predetermined distance known to correspond to the location of the weld 28. Alternatively, a transducer signal from the transducer unit 48 may be monitored as the mast extends and a characteristic change in the signal may be used to determine when the transducer unit is adjacent the weld 28. Transducer signals, as well as power and control signals for the crawler body and masts, are conveyed through an umbilical connection that comprises power and signal wires extending from the body 42 to a power and control unit 54, external to the reactor.

As the crawler moves about the diffuser, the ultrasonic transducer units 48, 50, 51 interrogate the welds 28, 30, 34 using ultrasonic emissions and collect ultrasonic signal reflections from the welds. These ultrasonic signal reflections are analyzed to determine the quality of the welds, and whether fatigue fractures or other defects exists in the welds. The crawler 40 indexes its movement around the diffuser so that its position is precisely known at each angular position around the diffuser. Accurate information regarding the crawler position is used to determine the location of the weld being inspected by the sensors supported by the crawler. Further, accurate transducer unit elevation information is collected by crawler body 42 as it moves up and down the mast shaft 46 for each transducer unit. The transducer units may be cyclically moved up and down to vertically traverse a weld as the crawler body slowly moves around the diffuser in a horizontal plane.

As shown in FIG. 3, conveying posts 56 on the crawler body allow hooks on a carriage (not shown) to lower the crawler 40 down into the reactor in the gap between the reactor pressure wall 14 (FIG. 1) and the reactor core wall 16. The crawler body 42 has a width (W), height (H) and an arc-shaped length (L). The crawler is lowered until tracking wheels 58 on one or both sides of the crawler body rest on the upper surface of the baffle plate. The tracking wheel 58 is rotationally coupled to an encoder 60 that monitors the rotation of the wheel and outputs a signal that can be converted to the distance traversed by the crawler body. The tracking wheel 58 may not be driven and may be turned by the movement of the crawler body across the baffle plate surface.

The crawler body 42 has an inside wall surface 62 that faces the tail pipe diffuser and an outer wall side 66, opposite to the inner side. The inner side is generally rectangular in plan view and is has an arc shaped cross-section. The arc of the body 42 corresponds to an arc from the circumference of the tail pipe diffuser, as is shown in FIG. 4. The crawler body is intended to seat against the outer side surface of the tail pipe diffuser 22 (FIG. 5) as the body circumnavigates the diffuser.

In one embodiment, the crawler body may form an arc of approximately 84°. The inner wall 62 of the crawler body is curved to conform substantially to the outer wall of the diffuser housing, e.g. the tail pipe. The outer wall 64 of the crawler body may be similarly curved. In one embodiment, the height (H) of the crawler body may be approximately seven inches (18 cm), the width (W) may be 1.2 inches (3 cm), and the length (L) across the arc of the body may be 16 inches (41 cm).

The crawler body provides a support frame for the mast modules 70 and a center driver module 64. The mast modules each support a mast 46 and transducer unit. The driver module 64 includes driving rollers 66. The modules are mounted in a frame of the crawler body. The frame includes an upper support plate 72 to which each of the modules is attached, e.g., bolted. Further, the conveying posts 56 may be attached to the outermost modules 70 and a tracking wheel assembly and encoder 58 may be attached to a lower corner of one of the outermost modules 70.

The crawler body includes a wiring harnesses 62 and passages for the sensor wires, power wires and other wires 64 from the transducers to a common wiring outlet 66 which may include a plug. The plug connects to an umbilical cord 68 which connects the sensor wires and power wires in the crawler body to an external instrument and power source and control device.

The crawler body supports three mast modules 70 each having a mast 46 and one of the ultrasonic transducer units 48, 50 and 51. Each mast module includes wiring for the sensor signals, control actuators and a motor 78 to operate the transducer and mast. The movement of the mast is precisely controlled such that the ultrasonic transducer at a distal end of the mast is accurately positioned with respect to the crawler body.

Figure 6:
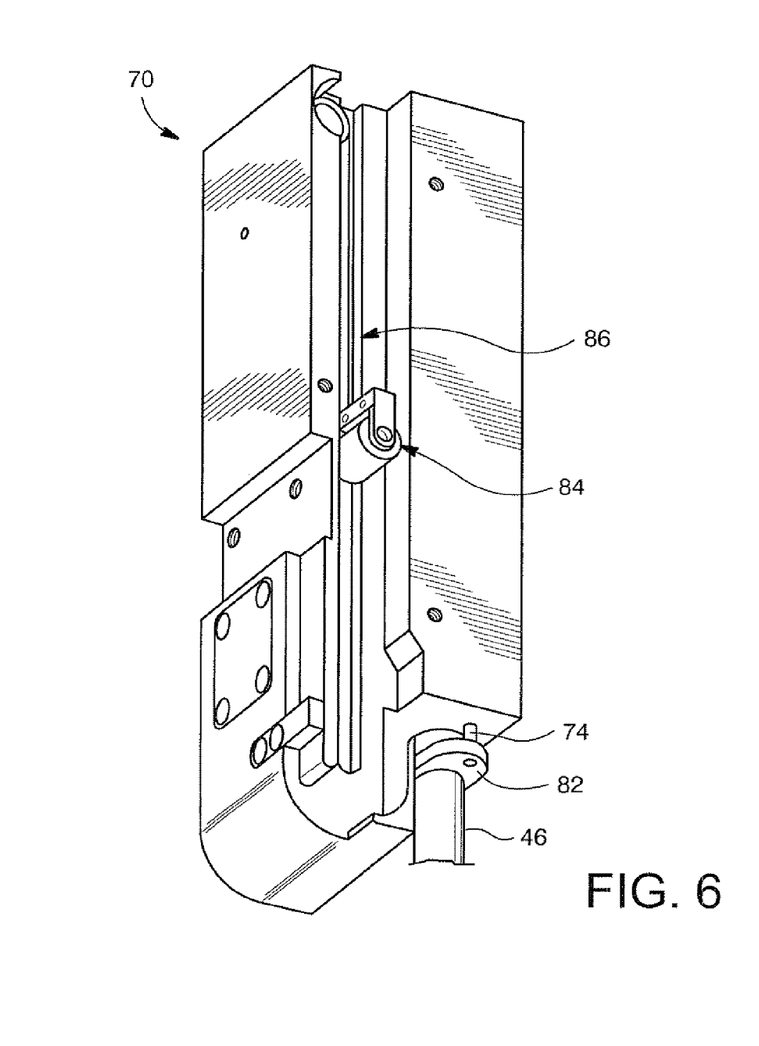
FIG. 6 a perspective view of a mast module for the crawler device.
Figure 7:
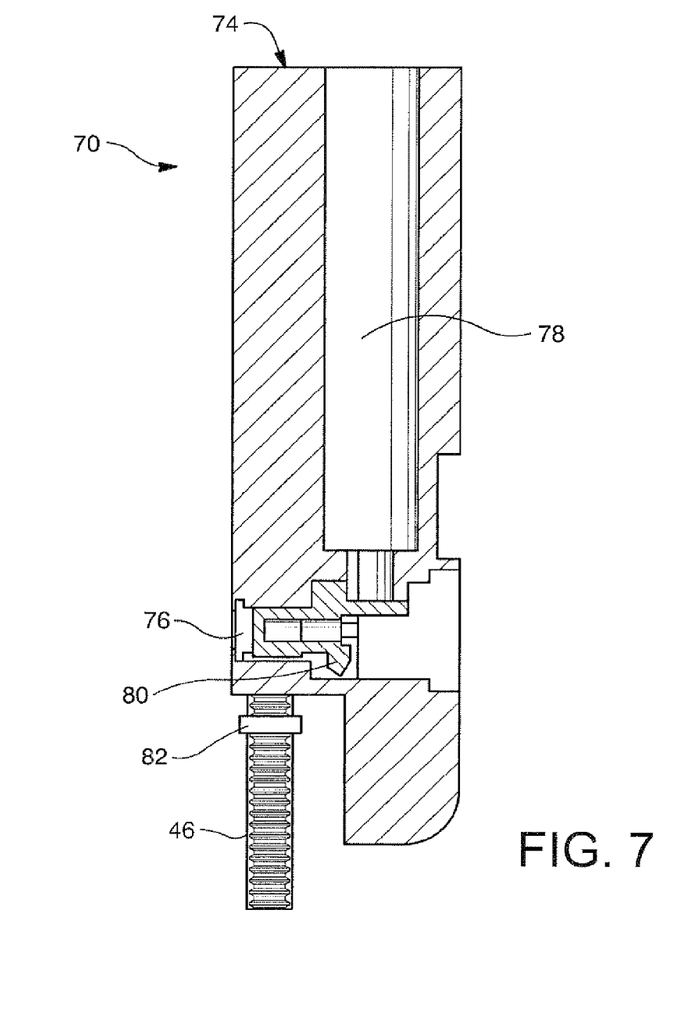
FIG. 7 is a cross-sectional view of the mast module.

FIG. 6 a perspective view of a mast module 70 for the crawler device and FIG. 7 is a cross-sectional view of the mast module 70. The module is a generally rectangular block having an aperture 74 extending vertically through the block to receive the sensor mast. The mast moves up and down through the aperture module 70. The mast shaft has gear teeth that engage a rotating gear wheel 76 in the mast module. A motor 78 drives the gear wheel 76 through bevel gears 80. The motor may be powered through the umbilical cord or by batteries. The power and control unit 54 (FIG. 5) may provide power for the motor, control signals to actuate the motor to raise or lower the mast shaft, and receive displacement signals that indicate the movement of the shaft 46 and thus the elevation of the transducer unit. A collar 82 is adjustably attached to the shaft to ensure that the transducer unit is not raised beyond a predetermined elevation.

A roller 84 slides up and down in a slot 86 in the side of the mast module 70. The roller assists in managing the cables used for control, power and sensor signal transmission with the transducer units 48, 50, 51. In each mast module, a cable for the transducer unit is looped over the roller 84. As the mast is extended, the roller moves upward to reduce the length of cable looped in the slot 86 and to allow cable to be extended with the mast. As the mast is retracted, the roller moves downward to pull up the cable and temporarily store a section of the cable in the slot 86.

Figure 8:
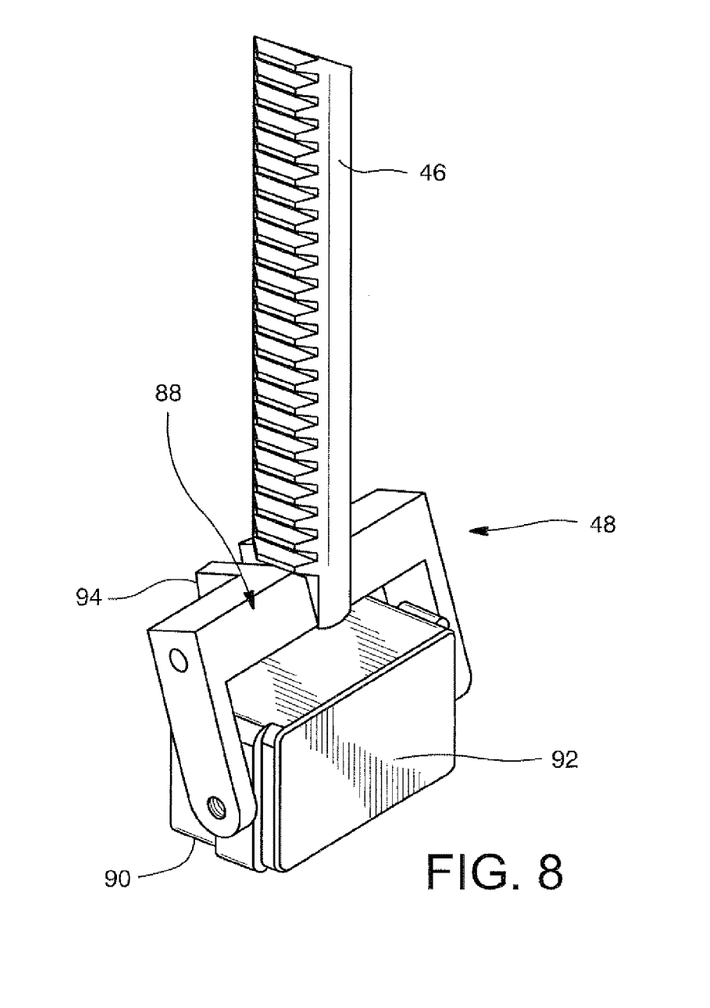
FIG. 8 is an enlarged perspective side view of a mast and scanner transducer.
Figure 9:
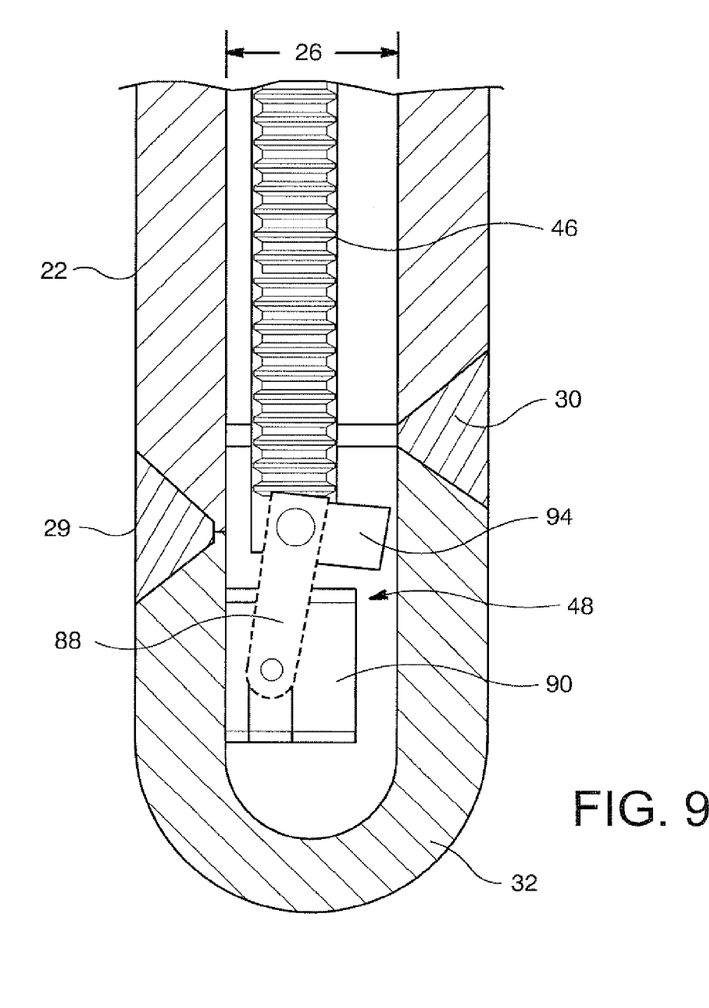
FIG. 9 is an enlarged side view of a mast and scanner transducer extended into a cross-section of the gap between a diffuser tail pipe and adapter ring.

FIG. 8 is an enlarged side view of a distal end of a mast 46 and scanner transducer unit 48 (but could be 50 or 51) and FIG. 9 shows the mast and transducer unit extended down into a gap between a diffuser tail pipe and adapter. The transducer unit includes a yolk 88 and a transducer sensor head 90. The yolk 88 is pivotably attached to a distal end of the mast 46. Arms on the yolk fit around and support the transducer sensor head 90 which pivots so that the face 92 of the head is adjacent the surface being inspected. A post 94 on the back of the yoke prevents the sensor head from abutting against the wall surface opposite the wall and weld being inspected. The yolk pivots the sensor head 90 such that the sensor face 92 is adjacent, e.g., abuts, the wall surface 22, 32, and weld 28 to be inspected. The yolks on the other masts each similarly pivot a face of a sensor head against a corresponding wall surface and weld.

Figure 10:
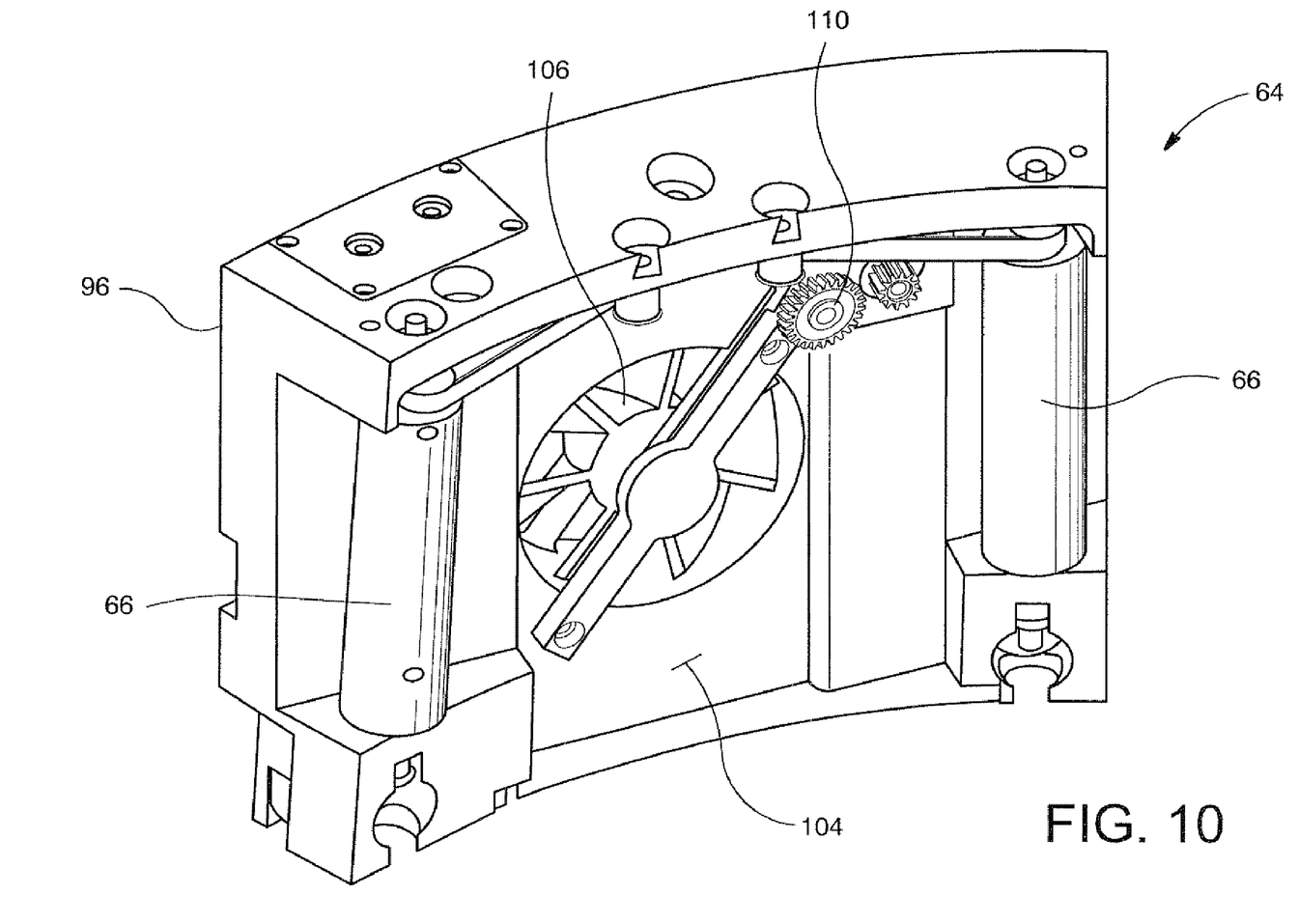
FIG. 10 is a perspective view of a first side of a driver module for the crawler body including drive rollers and a suction fan.
Figure 11:
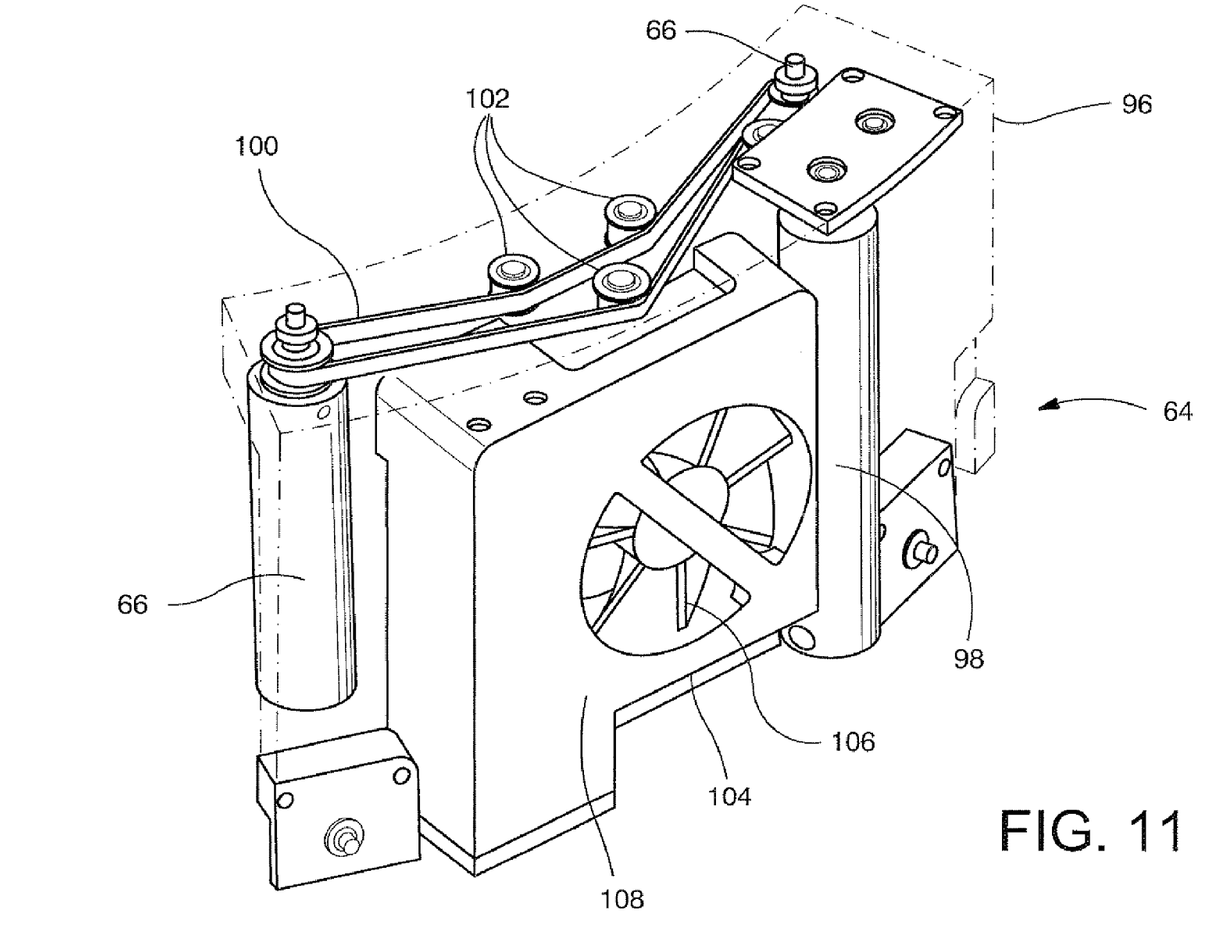
FIG. 11 is a perspective view of a second side of a driver module for the crawler with the frame of the module illustrated in outline to show the internal components of the body.

FIG. 10 is a rear perspective view of the driver module 64 and FIG. 11 is a front perspective view of the driver module with the internal components of the driver visible in the driver housing 96. The housing is generally rectangular and has a arc-shape to conform to the crawler body and tail pipe diffuser. The driver module 64 may be mounted in a center section of the crawler body. The driver module includes a pair of rotating drive rollers 66 mounted vertically and on opposite sides of the module. The drive rollers engage the surface of the tail pipe to move the crawler around the tail pipe. The drive rollers 66 may extend more than one-half the length of the height of the crawler body to provide good traction between the rollers and tail pipe surface. The rollers 66 extend partially out of the crawler body and past the inside surface 62 to the body so that they may engage the tail pipe.

The drive rollers are powered by a motor 98 internal to the drive module 64. A drive belt 100 or chain is moved by the motor and turns both rollers at a common speed. Rollers 102, including a tension roller, guide the belt between the motor and rollers and ensure that the belt is under an appropriate amount of tension. The motor for the rollers may receive power through the umbilical cord 52 or from batteries. The motor and/or the gearing for the drive belt are actuated by control signals from the power and control unit 54.

The drive module includes a suction module 104 mounted between the rollers. The suction module creates a slight suction between the crawler body and diffuser to ensure that the crawler body properly seats against the diffuser wall, e.g., tail pipe. The suction module includes an impeller 106 in an annular shroud housing 108. The impeller is rotatably mounted in the suction module and is driven by a belt extending from the impeller axis to a gear 110 that engages a drive gear powered by a motor in the suction module, e.g., horizontally mounted in the module above the impeller. The impeller 106 creates a slight suction between the inner wall of the crawler body and the wall of the diffuser tail pipe. The motor for the impeller may receive power through the umbilical cord or from batteries. The motor and/or the impeller gearing are actuated by control signals from the power and control unit 54.

In operation, the crawler 40 may be used when the reactor is opened for refueling. The robotic crawler body 42 is lowered into the gap 26 between the reactor pressure wall 14 and core 16, and positioned on the baffle plate 12 and abutting against a tail pipe 22 of a diffuser for a jet spray pump. The umbilical cord 52 from the crawler body 42 is connected to the power and control unit to provide power to the crawler body, and to establish control and communication with the crawler body. The impeller 108 is started to seat the crawler against the diffuser tail pipe.

A technician operates the crawler through the power and control unit 54. The masts 46 of the crawler body are lowered to position the transducer units 48, 50 and 51, adjacent each of the weld to be inspected. The crawler body may be positioned at particular angular position around the diffuser so that the initial position of the crawler can be determined. The technician confirms that appropriate signals are being received from each of the transducer units and that the crawler is properly communicating with the control unit. The technician commands the drive motor 98 to be actuated and the crawler slowly moves around the diffuser. As the crawler moves, the welds 28, 30, 34 are interrogated with ultrasonic signals from a respective one of the transducer units. The reflected signals from the welds are analyzed and captured by the computer control unit 54, and may be displayed on a computer screen for viewing by the technician. The crawler may move the masts and transducer units up and down to sweep the surfaces of the welds as the crawler moves around the diffuser. The movement of the crawler is measured by the tracking wheel 58 that rolls across the baffle plate. An encoder on the tracking wheel generates displacement signals indicating the distance traveled by the crawler body. The weld inspection is completed for a diffuser when the crawler body has traversed the entire circumference of a diffuser tail pipe. The crawler body may be lifted and shifted to another diffuser tail pipe where another weld inspection is performed.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An inspection assembly adapted to traverse an inspection surface, said assembly comprising:
   a crawler body including a first side and a bottom side, wherein the first side is adapted to face an upright surface and a bottom side is adapted to engage a horizontal surface and seperated from the first inspection surface by a gap;
   a suction module in the crawler body adapted to create a suction between the vertical surface and the first side of the crawler, wherein the suction biases the crawler body against the vertical surface;
   at least one roller mounted on the crawler body adapted to engage the horizontal surface, and
   at least one mast having a mount to receive a sensor, wherein said mast extends from the crawler body into the gap between the vertical surface and the horizontal surface.

2. An inspection assembly as in claim 1 wherein the sensor is at least one of an ultrasonic transducer, an Eddy current sensor and an image capture device.

3. A inspection assembly as in claim 1 wherein the upright surface is substantially circular in cross section, the first side of the crawler body is arc-shaped to conform to the upright surface, and the gap is annular.

4. An inspection assembly as in claim 1 further comprising a driver module including at least one driver roller extending through the first side of the crawler body and adapted to engage the upright surface.

5. An inspection assembly as in claim 1 wherein the suction module includes an impeller adapted to create a suction between the first side of the crawler body and the upright surface.

6. An inspection assembly as in claim 1 further comprising a tracking wheel mounted on the crawler body and engaging the horizontal surface, and an encoder generating a signal indicative of displacement of the tracking wheel.

7. An inspection assembly adapted to traverse an inspection surface, said assembly comprising:
   a crawler body including a first side and a bottom side, wherein the first side adapted to face a first inspection surface and the bottom side is adapted to engage a second inspection surface seperated from the first inspection surface by a gap, wherein the first inspection surface is upright and the second inpection surface is sudstantially horizontal;
   a suction module in the crawler body adapted to create a suction between the first inspection surface and the first surface of the crawler, wherein the suction biases the crawler body against the first inspection surface;
   at least one roller mounted on the crawler body adapted to engage the first inspection surface, and
   at least one mast having a mount to receive a sensor, wherein said mast extends from the crawler body into the gap.

8. An inspection assembly adapted to inspect welds associated with a diffuser in a jet pump in a boiling water nuclear reactor (BWR), the assembly comprising:
   a crawler housing including a first side surface and a bottom surface, wherein the first side surface faces a side surface of the diffuser and the bottom surface faces a baffle plate of the BWR;
   a suction device in the first side surface adapted to create a suction between the first side surface and the side surface of the diffuser to bias the crawler body against the diffuser, and
   at least one mast having a mount to receive a sensor and said mast extending from the crawler housing down through an annular gap between the baffle plate and diffuser.

9. An inspection assembly as in claim 8 wherein the sensor is at least one of an ultrasonic transducer, an Eddy current sensor and an image capture device.

10. A inspection assembly as in claim 8 wherein the at least one mast is a plurality of masts including a first mast has a sensor facing outward of the BWR and a second mast has a sensor facing inward of the BWR.

11. A inspection assembly as in claim 8 wherein the surface of the diffuser is substantially circular in cross section, and the first side of the crawler body is arc-shaped to conform to the surface of the diffuser.

12. An inspection assembly as in claim 8 further comprising a driver module including at least one driver roller extending through the first side of the crawler body and adapted to engage the surface of the diffuser.

13. An inspection assembly as in claim 8 wherein the suction module includes an impeller adapted to create a suction between the first side of the crawler body and the side surface of the diffuser.

14. An inspection assembly as in claim 8 further comprising a tracking wheel mounted on the crawler body and adapted to engage the baffle plate, and an encoder generating a signal indicative of displacement of the tracking wheel.

15. A method for inspecting weld joints in a gap between an generally horizontal surface and a generally upright surface using a robotic crawler including a crawler body having at least one mast and a sensor mounted on the mast, said method comprising:
   positioning the crawler body on the horizontal surface and against the upright surface;
   establishing a suction between the crawler body and upright surface to seat the body against the upright surface;
   extending the mast and sensor into the gap below the crawler body;
   moving the crawler body across the horizontal surface while the suction seats the body against the upright surface, and
   sensing a condition in the gap with the sensor and conveying signals from the sensor to a control unit.

16. A method as in claim 15 further comprising driving the movement of the crawler body with drive rollers extending from the crawler body and engaging the upright surface.

17. A method as in claim 15 wherein the upright surface is circular in cross-section and the movement of the crawler body is a circular movement around the upright surface.

18. A method as in claim 15 wherein the sensor is at least one of an ultrasonic transducer, an Eddy current sensor and an image capture device, and the condition in the gap is a welded joint on a side surface of the gap.

19. A method as in claim 15 further comprising lowering the crawler body to the horizontal surface and down between opposing walls, and extending includes lowering thee mast and sensor from the crawler body down into the gap.

20. A method as in claim 19 wherein the opposing walls are a boiling water reactor pressure wall and a core wall, the upright surface is a diffuser tail pipe of a jet spray pump, and the horizontal surface is a baffle plate, wherein the movement of the crawler body is a circular movement around the diffuser tail pipe.

* * * * *

UNITED STATES PATENT AND TRADEMARK OFFICE
CERTIFICATE OF CORRECTION

PATENT NO. : 7,587,942 B2  Page 1 of 1
APPLICATION NO. : 11/564415
DATED : September 15, 2009
INVENTOR(S) : Brandon Smith et al.

It is certified that error appears in the above-identified patent and that said Letters Patent is hereby corrected as shown below:

In the Claims:

Col. 7, line 6, delete "a bottom" and insert --the bottom--

Col. 7, line 7, delete "seperated" and insert --separated--

Col. 7, line 41, insert --is-- between "first side" and "adapted"

Col. 7, line 43, delete "seperated" and insert --separated--

Col. 7, lines 45-46, delete "inpection surface is sudstan-tially" and insert --inspection surface is substan-tially--

Col. 7, line 60, delete "sufface" and insert --surface--

Signed and Sealed this

Third Day of November, 2009

David J. Kappos
*Director of the United States Patent and Trademark Office*